United States Patent [19]

Debabov et al.

[11] Patent Number: 4,680,260
[45] Date of Patent: Jul. 14, 1987

[54] METHOD FOR PRODUCING HUMAN LEUKOCYTE INTERFERON ALPHA-2

[75] Inventors: Vladimir G. Debabov; Jury D. Tsygankov, both of Moscow; Andrei J. Chistoserdov, Moskoskaya oblast; Evgeny D. Sverdlov, Moscow; Lara S. Izotova, Moscow; Sergei V. Kostrov, Moscow; Viktor E. Sterkin, Moscow; Vladimir P. Kuznetsov, Moscow; Sergei V. Belyaev, Moscow; Galina S. Monastyrskaya, Moscow; Irina S. Salomatina, Moscow; Grigory M. Dolganov, Moscow; Sergei G. Arsenian, Moscow; Sergei A. Tsarev, Moscow; Jury I. Kozlov, Moscow; Alexandr Y. Strongin, Moscow; Vsevolod I. Ogarkov, Moscow; Jury A. Ovchinnikov, Moscow, all of U.S.S.R.

[73] Assignee: Vsesojuzny Nauchno-Issledovatelsky Institut Genetiki, Mowcow, U.S.S.R.

[21] Appl. No.: 751,798

[22] Filed: Jul. 3, 1985

[30] Foreign Application Priority Data

Jul. 13, 1984 [SU] U.S.S.R. .............................. 3757952

[51] Int. Cl.$^4$ .................. C12P 21/00; A61K 45/02
[52] U.S. Cl. ................................... 435/68; 435/811; 424/85
[58] Field of Search ............... 435/68, 172.3; 424/85; 260/112.5 P

[56] References Cited

FOREIGN PATENT DOCUMENTS 62971 10/1982 European Pat. Off. .
2079291 1/1982 United Kingdom .

*Primary Examiner*—Blondel Hazel
*Attorney, Agent, or Firm*—Burgess, Ryan & Wayne

[57] ABSTRACT

A method for producing human leukocyte interferon alpha-2 resides in that there is carried out submerged cultivation of a producer strain Pseudomonas species VG-84 carrying a plasmid pVG3 with an inserted gene of human leukocyte interferon alpha-2, said strain being deposited in the collection of microorganism cultures at the USSR Antibiotics Research Institute under Reg. No. 1742; said strain being cultivated in a nutrient medium, containing the sources of carbon and nitrogen, mineral salts and growth stimulants, under aeration in the presence of antibiotics, i.e., streptomycin or tetracycline, or a mixture of both, followed by isolation and purification of the end product.

2 Claims, 1 Drawing Figure

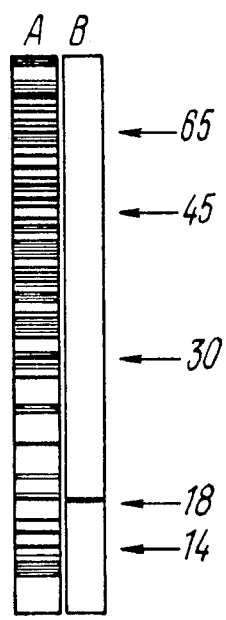

METHOD FOR PRODUCING HUMAN LEUKOCYTE INTERFERON ALPHA-2

FIELD OF THE INVENTION

The present invention relates to microbiological field and has particular reference to production of human leukocyte interferon alpha-2 featuring antiviral activity and having application in medicine for prevention and treatment of some widely spread diseases of the viral etiology.

BACKGROUND OF THE INVENTION

Interferons are in fact proteins synthesized by specific human cells in response to a viral infection. Depending upon the type of a cell-producer and specific structural and functional features of interferons they can be subdivided into three basic types, that is, alpha or leukocyte interferon produced by leukocytes, beta or fibroblast interferon produced by fibroblasts, and gamma or immune interferon produced by T-lymphocytes.

Apart from their antiviral activity interferons also feature antiproliferative activity and also effect the immune response. This enables one to regard drugs based on interferon as a potentially effective means for treatment of some malignant neoplasms. By now highly-purified preparations of human interferon have been produced, which are in effect a family of 13 to 15 closely related proteins, each being coded with its own structural gene in chromosome 9. However, isolation of leukocyte interferon from donor's blood fails to provide its production in an amount sufficient for extensive clinical application, since the interferon content of liter of blood is as a rule within $10^5$ AU, whereas a single effective dose of interferon intended for intravenous injection to a patient, amounts to at least $10^6$ AU proceeding from tentative clinical observations.

Known in the present state of the art are diverse methods for producing human leukocyte interferons, based on the use of a variety of strains of microorganisms as producer strains, into which individual genes of human interferon have been transferred by means of vector molecules. In particular, use is made of bacterial strains of *Escherichia coli, Bacillus subtilis, Methylophilus methylotrophus*, etc. as the producer strains (cf. European Patent EP No. 0062971A2, published in 1982, Int.Cl$^3$. C 12N 15/00).

Microorganisms containing a plasmid with the inserted gene of human leukocyte interferon, produce interferon when cultivated under submerged aerobic conditions in nutrient media containing assimilable sources of carbon and nitrogen, mineral salts and growth factors.

Known in the art is a method for producing human leukocyte interferon alpha-2 (cf. British Pat. No. 2,079,291A, published in 1982, Cl. C 12N 15/00), wherein use is made of *E. coli* K-12, strain 294, obtained by inserting a recombinant plasmid pLeIFAtrp 2,5, wherein the gene of interferon alpha-2 is under control of the regulator regions of a tryptophane operon of *E. coli*.

The aforesaid strain is cultivated under submerged conditions in nutrient media, containing the sources of carbon and nitrogen, mineral salts and growth stimulants, in the presence of an antiobiotic.

The interferon yield, for the aforesaid producer, amounts to $2.5 \times 10^8$ AU per liter of the culture liquid.

However, application of *E. coli* as an industrial producer suffers from some disadvantages. *E. coli* is assumed to be a conventionally pathogenic microorganism, although the various strains of this bacterium are permanently present in the intestinal microflora of human beings. This fact imposes especially stringent requirements upon purification of drugs produced on the base of *E. coli* and complete separation of the protein impurities and endotoxins, which in turn makes the interferon production process much more expensive and affects adversely the yield of pure end product. Moreover, all the heretofore-known laboratory strains of *E. coli* are susceptible to phagolysis, the number identified phages specific for *E. coli* amounting to several hundreds.

In addition, the method discussed above suffers also from a relative low productivity of the culture, whereby interferon isolation from the cellular biomass and its subsequent purification until a homogeneous state is obtained, is a labour-consuming procedure.

SUMMARY OF THE INVENTION

It is a primary object of the present invention to provide a higher yield of human leukocyte interferon alpha-2 and simplified process for its isolation.

The aforesaid object of the invention is accomplished due to the fact that in a method for producing human leukocyte interferon alpha-2 by virtue of submerged cultivation of a producer strain, incorporating a plasmid with an inserted gene of human leukocyte interferon alpha-2, in a nutrient medium containing the sources of carbon and nitrogen, mineral salts and growth stimulants under aeration in the presence of an antibiotic, followed by isolation and purification of the end product, according to the invention, used as a producer strain is the strain of Pseudomonas species VG-84 carrying a plasmid pVG-3 and deposited in the collection of microorganisms cultures at the USSR Antibiotics Research Institute under Reg. No. 1742 said producer being cultivated in the presence of antibiotics, i.e., streptomycin or tetracycline, or a mixture of both; it is preferable that tetracycline be applied in an amount of 30 to 50 mg/l, and streptomycin, in an amount of 50 to 150 mg/l.

The method of the invention is instrumental, due to the use of a novel highly productive strain of Pseudomona species VG-84, in attaining a higher yield of the end product and a simplified process for its isolation.

DETAILED DESCRIPTION OF THE INVENTION

According to the method of the invention, use is made of a novel strain of Pseudomonas special VG-84, wherein the gene of human leukocyte interferon alpha-2 has been cloned, as part of a multicopy plasmid pVG3 under control of the regulator regions of gene D of bacteriophage $\phi$X174.

The plasmid pVG3 is a molecular hybrid of a multicopy vector plasmid pAYC34 of a wide range of hosts, and a plasmid pIFN-$\alpha$2-P2, incorporating a replicon pBR 322 and a gene of interferon alpha-2, and responsible for cell resistance to tetracycline and ampicillin. The gene of interferon alpha-2 in the plasmid pIFN-$\alpha$2-P2 is under control of the regulator regions of a gene D of the bacteriophage $\phi$X174. The vector plasmid PAYC34 of 9.4 thousand base pairs, relates to an incompatibility group Inc p-4/Q and determines cell resistance to streptomycin. The plasmid pAYC34 and pIFN-α2-P2 DNA was treated with Pst 1, whereupon the competent cells of the *E. coli* strain C600 was transformed with the ligated mixture. Then the transformants were selected on a complete nutrient medium, containing antibiotics, i.e., amplicillin (50 μ/ml), streptomycin (100 μ/ml) and tetracycline (25 μ/ml). There was found in the transformant-clones a plasmid DNA named pVG3, which corresponds, as for size and restriction map, to a hybrid of the plasmids pAYC34 and pIFN-α2-P2. The plasmid pVG3 determines the cell resistance to streptomycin as the pAYC34 does, and to tetracycline and amplicillin like the pIFNα-2-P2. The size of the plasmid pVG3 equals to 14.8 thousand base pairs and makes up the sum of the plasmids pIFN-α2-P2 (5.4 thousand base pairs and pAYC34 (9.4 thousand pairs of nucleotides).

A conjugative wide-hose range plasmid R 751 was inserted in one of the *E. coli* strains C600 containing the hybrid plasmid pVG3. It is through a series of conjugative cross that the plasmid pVG3 was transferred into bacteria of genus Pseudomonas, and some other Gram-negative bacteria. Then transconjugant bacteria were taken out of a selective medium containing the aforementioned antibiotics and tested for ability to synthesize interferon.

The cultures obtained by the aforedescribed method are then cultivated under aeration and stirring at 30° in L-broth within 6 to 10 hours until a cell density of 2 to $5\times10^9$ cells/ml was obtained. Then the bacteria were collected by centrifugation, disrupted ultrasonically, and the interferon content of the cell extracts was determined by the radioimmunoassay. A total of 18 strains of Gram-negative bacteria relating to the genus Escherichia, Salmonella, Pseudomonas, Methylomonas, Erwinia, and Rhizobium were treated. The majority of the strains tested were found to produce active interferon. It was the strain of Pseudomonas sp. VG-84 that was characteristic of the greatest productivity. Thus, under the aforedescribed conditions, the strain was found to produce $5\times10^9$ to $1\times10^{10}$ AU of interferon per liter of the culture liquid.

The strain of Pseudomona sp. VG-84 has been deposited in the collection of microorganism cultures at the USSR Antibiotics Research Institute under Reg. No. 1742. The growth and morphological characteristics of the strain Pseudomonas sp. VG-84 carrying the plasmid pVG3 are as follows:

| Microscopy morphology | Motile Gram-negative rod-cells 3 to 5 μm long |
|---|---|
| Morphology in various media: | |
| Beef-extract agar | Upon a 24-hour cultivation period at 25 to 30° C. forms dia. 3 to 4 mm rough irregularly edged colonies featuring rough surface and light-green colour. |
| Beef-extract broth | Exhibits moderate growth upon thrust inoculation, principally on the surface of the culture medium (substrate). Grows weakly without aeration. |
| Minimal nutrient medium M9 with glucose | Forms dia. 2 to 3 mm round, rough, grey-coloured colonies on the second day of cultivation. |
| Physiological and biochemical characteristics | Grows at 25 to 35° C., optimally at 30° C., pH = 7.0. Carbon sources - utilizes glucose and arabinose. |
| | Nitrogen sources: assimilates well. Requires adenine. Resistant to streptomycin and tetracycline. |

The method of the invention is carried into effect as follows. The strain of Pseudomonas sp. VG-84 is cultivated in an agar-doped nutrient medium at 28° to 30° C. for 8 to 12 hours, whereupon it is reinoculated into a liquid nutrient medium, and the inoculum is cultivated under intense stirring and aeration for 3 to 6 hours at 28° C. Fermentation is conducted in a fermentation apparatus in any liquid nutrient medium suitable for the purpose and containing the sources of carbon and nitrogen, mineral salts and growth factors, e.g., in a nutrient medium containing glucose, yeast extract or autolysate, or tripton, or pepton, or hydrolysates of casein or of yeast, or a mixture thereof. Fermentation is carried out in the presence of antibiotics, i.e., streptomycin or tetracycline, or a mixture of both. It is preferable that tetracycline be used in amount of 30 to 50 mg/l and streptomycin, 50 to 150 mg/l. The fermentation process runs for 6 to 10 hours at 28° to 32° C. and the pH value within 6.7 and 7.1 under vigorous aeration. An optical density $A_{550}$ of the bacterial suspension is measured in the course of fermentation, the value of the optical density amounting to 5 or 7 optical units by the end of the fermentation process.

Under the aforedescribed cultivation conditions the yield of interferon, as evidenced by radioimmunoassay or by determining its antiviral activity on human fibroblast cell culture, ranges within $5\times10^9$ and $1.5\times10^{10}$ AU per liter of the culture liquid.

On completing the fermentation process and attaining the aforesaid optical density, bacterial cells are collected by centrifugation, resuspended in an appropriate buffer and disrupted with the aid of ultrasonic treatment, or by any other technique resulting in disintegration of the cells or breaking the cell membrane, e.g., treatment with lysozyme, application of the ballistic techniques involving the use of glass or metallic balls, making use of a French press, and the like. Then the cell debris is separated by centrifugation, whereupon interferon is isolated from the supernatant fraction, which is in fact the cell extract, using the known techniques of protein fractionation and purification. The yield of homogeneous interferon as shown by various physico-chemical methods, ranges within 20 and 60 percent, the purification ratio being within 200 to 500 fold and specific activity of the thus-purified end product equalling $4\times10^8$ AU. The course of purification is monitored by determining the antiviral activity of interferon on human fibroblast cell cultures with vesicular stomatitis virus as a challenge RIA or ELISA. The purity of interferon preparations resulting from purification is tested with immunological, electrophoretic, gel-filtration and sedimentation techniques, as well as by determining the amino-acid composition and the N-terminal aminoacid sequence of the isolated end product. The thus-obtained homogeneous preparations of human leukocyte interferon alpha-2 exhibit the entire set of specific structural and functional features specific to this type of interferon.

The method of the invention is advantageous over the known method in that a high level of activity is attainable due to application of a novel highly productive strain. Thus, the same amount of interferon can be obtained from a lower amount of biomass, which contributes to reduced expenses for biomass isolation and disintegration, as well as for all subsequent operations involved in producing a homogeneous product.

According to data obtained from Edman automatic N-terminal sequence determination homogeneous interferon isolated from the biomass of the producer strain of Pseudomonas sp. VG-84 features the N-termination amino-acid sequence Cys-Asp-Leu-Pro-Glu-Thr-Mis-Ser-... and contains no N-terminal methionine residue, thus being completely identical to interferon alpha-2 produced by human leukocytes.

To promote understanding of the present invention given below are the following examples of practical embodiment of a method for producing human leukocyte interferon alpha-2.

EXAMPLE 1

The strain of Pseudomonas sp. VG-84 is cultivated at 28° C. for 12 hours on solid agar medium of the following composition: tripton, 10 g/l; yeast extract, 5 g/l; adenine, 80 mg/l; glucose, 10 g/l; streptomycin, 150 mg/l; tetracycline, 50 mg/l; distilled water, to make up one liter; agar-agar, 15 g/l. The biomass that has been cultivated on the aforesaid agar medium is used for preparation of the incoculum. To this end the biomass cells are transferred to 750-ml Erlenmeyer flasks containing 100 ml of culture medium specified above (agar-free), and are cultivated on a shaker for 6 hours under vigorous stirring (240 rpm) at 28° C. An optical density of the inoculation culture makes up two optical units.

The cultivation process is conducted in a fermentation apparatus equipped with the temperature, pH, stirring rate and aeration control systems, and a pressure sensor for measuring the partial pressure of dissolved oxygen. With this purpose in view the inoculation culture is inserted in a 5-percent proportion into the fermentation apparatus containing the nutrient substrate having the aforestated composition (agar-free) and is grown for 6 hours at $28+0.5°$ C., the pH value from 6.7 to 6.9 under intense aeration and stirring. The aeration and stirring conditions are so selected that the culture grown should not be limited to the concentration of dissolved oxygen, for which purpose the partial pressure of oxygen is maintained at a level of 5 to 10 percent of saturation. Ammonia liquor is used to stabilize the pH value.

The biomass growth is monitored by measuring the optical density of the culture liquid, which is determined as frequently as every hour. Fermentation ceases as soon as the optical density $A_{550}$ reaches five optical units.

The fermentation process over, the concentration of human leukocyte interferon alpha-2 is equal to $1.5 \times 10^{10}$ AU per liter of the culture liquid. In order to determine the concentration of the thus-obtained interferon, use is made of the solid-phase modification of RIA involving application of anti-interferon rabbit polyclonal antibodies and murine monoclonal antibodies labelled with $^{125}I$ isotope. In addition, antiviral interferon activity is determined by its protective effect towards cytopathic action of the vesicular stomatitis virus produced on cultures of human diploid fibroblasts. Used as reference preparations is an interferon standard MRC B69/19 (Great Britain).

The cells collected by centrifugation after fermenting is used as an interferon source. They are suspended in a 0.1M Tris-buffer having the pH value of 7.5 (1 g cells per 5 to 10 ml buffer), and destructed in an ultrasonic disintegrator. Then the cell debris is separated by centrifugation at 30,000 g, and homogeneous human leukocyte interferon alpha-2 is isolated from the supernatant fraction (cell extract).

As a result of subsequent purification, an electrophoretically homogeneous preparation of human leukocyte interferon alpha-2 is obtained, featuring the purification ratio of 210, a 41-percent yield (in terms of activity), and a specific activity of $4.0 \times 10^8$ AU. The appended drawing represents data of an electrophoretic analysis of human leukocyte interferon alpha-2, wherein shown under A is interferon preparation before purification, under B, interferon preparation after purification, while molecular weight of reference proteins is indicated (in terms of kD) with the figures on the right. Electrophoresis is carried out in 12.5-percent polyacrylamide gel in the presence of sodium dodecylsulphate. As to specific activity, molecular weight (18.4 kD), amino-acid composition, and other characteristics, the thus-isolated human leukocyte interferon alpha-2 differs in no respect from human leukocyte alpha-2 isolated from other bacterial producer strains.

EXAMPLE 2

The process is carried out similarly to that described in example 1. The producer is grown in the presence of antibiotics, i.e. streptomycin in an amount of 50 mg/l and tetracycline in an amount of 30 mg/l. After a six-hour fermentation process, an optical density of the bacterial suspension is equal to 4.2 optical units, while a liter of the culture liquid contains $7.5 \times 10^9$ AU of human leukocyte interferon alpha-2.

EXAMPLE 3

The process is conducted in the same way as described in Example 1, the producer being grown in the presence of an antibiotic tetracycline in an amount of 50 mg/l.

After 5.5-hour fermentation process, an optical density of the bacterial suspension equals 5.5 optical units, while interferon concentration per liter of the culture liquid is $9.5 \times 10^9$ AU.

What we claim is:

1. A method for producing human leukocyte interferon alpha-2, which comprises carrying out submerged cultivation of a producer strain Pseudomonas species VG-84 carrying a plasmid pVG3 with an inserted gene of human leukocyte interferon alpha-2, said strain being deposited in the collection of microorganism cultures at the USSR Antibiotics Research Institute under Reg. No. 1742; and strain being cultivated in a nutrient medium, containing the sources of carbon an nitrogen, mineral salts and growth stimulants, under aeration in the presence of streptomycin or tetracycline, or a mixture of both, followed by isolation and purification of the end product.

2. A method as claimed in claim 1, wherein tetracycline and streptomycin are used in an amount of 30 to 50 mg/l and 50 to 150 mg/l, respectively.

* * * * *